US009975094B2

(12) United States Patent
Gillis et al.

(10) Patent No.: US 9,975,094 B2
(45) Date of Patent: May 22, 2018

(54) REACTIVE FLOW STATIC MIXER WITH CROSS-FLOW OBSTRUCTIONS

(71) Applicant: Dow Global Technologies LLC, Midland, MI (US)

(72) Inventors: Paul A. Gillis, Lake Jackson, TX (US); Joydeep Mukherjee, Missouri City, TX (US); John B. Cooper, West Columbia, TX (US); Arthur C. Flores, Alvin, TX (US); Daniel J. Reed, Midland, MI (US)

(73) Assignee: Dow Global Technologies LLC

( * ) Notice: Subject to any disclaimer, the term of this patent is extended or adjusted under 35 U.S.C. 154(b) by 0 days. days.

(21) Appl. No.: 15/472,424

(22) Filed: Mar. 29, 2017

(65) Prior Publication Data

US 2017/0197189 A1    Jul. 13, 2017

Related U.S. Application Data

(63) Continuation of application No. 13/816,877, filed as application No. PCT/US2011/053583 on Sep. 28, 2011.

(Continued)

(51) Int. Cl.
*B01F 5/04* (2006.01)
*B01F 5/06* (2006.01)
(Continued)

(52) U.S. Cl.
CPC .......... *B01F 5/0485* (2013.01); *B01F 3/0865* (2013.01); *B01F 5/0473* (2013.01);
(Continued)

(58) Field of Classification Search
CPC .... B01F 5/0471; B01F 5/0473; B01F 5/0475; B01F 5/0602; B01F 5/0485; B01F 5/061;
(Continued)

(56) References Cited

U.S. PATENT DOCUMENTS 3,507,626 A    4/1970  Horn
4,128,569 A    12/1978 Horn et al.
(Continued)

FOREIGN PATENT DOCUMENTS

EP    1157726 A1     11/2001
EP    1302236 A1 *   4/2003    ............ B01F 5/0373
(Continued)

OTHER PUBLICATIONS

PCT/US2011/053583, International Search Report/Written Opinion of the International Searching Authority, dated Feb. 2, 2012. pp. 1-19.

(Continued)

*Primary Examiner* — Walter D. Griffin
*Assistant Examiner* — Marc C Howell

(57) ABSTRACT

Embodiments of the present invention relate to a mixing apparatus. Particularly, embodiments of the present invention provide a mixing apparatus for mixing fluid components such as phosgene and amine during a highly reactive chemical reaction. One embodiment provides a mixing conduit comprising a cylindrical sidewall defining an inner volume, wherein one or more jets are formed through the cylindrical sidewalls and connect to the inner volume and one or more flow obstructions disposed in the inner volume, wherein each flow obstruction is positioned upstream from an associated aperture.

6 Claims, 9 Drawing Sheets

Related U.S. Application Data

(60) Provisional application No. 61/387,229, filed on Sep. 28, 2010.

(51) Int. Cl.
*B01F 3/08* (2006.01)
*C07C 263/10* (2006.01)

(52) U.S. Cl.
CPC ............ *B01F 5/061* (2013.01); *C07C 263/10* (2013.01); *B01F 2005/0622* (2013.01); *B01F 2005/0623* (2013.01); *B01F 2005/0636* (2013.01); *B01F 2215/0036* (2013.01)

(58) Field of Classification Search
CPC ............ B01F 3/0865; B01F 2215/0036; B01F 2005/0622; B01F 2005/0623; B01F 2005/0636; C07C 263/10
USPC .................. 366/336, 337, 338, 178.2, 178.3
See application file for complete search history.

(56) References Cited

U.S. PATENT DOCUMENTS

| | | | |
|---|---|---|---|
| 4,264,212 A * | 4/1981 | Tookey | B01F 5/0403 239/433 |
| 4,289,732 A | 9/1981 | Bauer et al. | |
| 4,419,295 A | 12/1983 | Hennig et al. | |
| 4,692,030 A | 9/1987 | Tauscher et al. | |
| 4,929,088 A | 5/1990 | Smith | |
| 4,981,368 A | 1/1991 | Smith | |
| 5,117,048 A | 5/1992 | Zaby et al. | |
| 5,314,506 A | 5/1994 | Midler, Jr. et al. | |
| 5,516,935 A | 5/1996 | Bischof et al. | |
| 5,839,828 A | 11/1998 | Glanville | |
| 5,845,993 A | 12/1998 | Shirtum et al. | |
| 5,931,579 A | 8/1999 | Gallus et al. | |
| 6,264,900 B1 | 7/2001 | Schubert et al. | |
| 6,558,435 B2 | 5/2003 | Am Ende et al. | |
| 6,726,354 B1 | 4/2004 | Breuer et al. | |
| 6,838,578 B2 | 1/2005 | Leimkuhler et al. | |
| 7,118,920 B2 | 10/2006 | Brophy et al. | |
| 7,901,128 B2 | 3/2011 | Gehrke et al. | |
| 9,259,704 B2 | 2/2016 | Gillis et al. | |
| 2002/0121350 A1 * | 9/2002 | Lamminen | B01F 5/0473 162/100 |
| 2002/0191483 A1 | 12/2002 | Ohtsuki et al. | |
| 2004/0057334 A1 | 3/2004 | Wilmer et al. | |
| 2006/0245296 A1 * | 11/2006 | Nishioka | B01D 53/8631 366/174.1 |
| 2006/0252961 A1 | 11/2006 | Adachi et al. | |
| 2007/0177452 A1 | 8/2007 | Aroussi | |
| 2008/0087348 A1 * | 4/2008 | Gillis | B01F 5/0475 137/896 |
| 2008/0232190 A1 * | 9/2008 | Schneider | B01F 5/0619 366/337 |
| 2009/0103393 A1 | 4/2009 | Moser et al. | |
| 2010/0137634 A1 * | 6/2010 | Ding | B01F 5/0473 560/347 |
| 2011/0228630 A1 | 9/2011 | Gillis et al. | |
| 2011/0251425 A1 | 10/2011 | Penzel et al. | |

FOREIGN PATENT DOCUMENTS

| | | | |
|---|---|---|---|
| JP | 50009859 | 6/1973 | |
| JP | 50022346 | 7/1973 | |
| JP | 56028695 | 3/1981 | |
| JP | 57048954 | 3/1982 | |
| JP | 57165226 | 10/1982 | |
| JP | 58036626 | 3/1983 | |
| JP | 62128910 | 6/1987 | |
| JP | 06074423 | 3/1994 | |
| JP | 2007332797 A | 12/2007 | |
| JP | 2008049306 A | 3/2008 | |
| JP | 5067325 B2 | 11/2012 | |
| WO | 00/12202 A1 | 3/2000 | |
| WO | 2008/000616 A2 | 1/2008 | |
| WO | WO 2011138162 A1 * | 11/2011 | ............ B01F 5/0471 |

OTHER PUBLICATIONS

PCT/ US2011/053583, International Preliminary Report on Patentability, dated Apr. 2, 2013, pp. 1-12.

Japanese Office Action for JP2013-530430, dated Apr. 28, 2015, pp. 1-6.

* cited by examiner

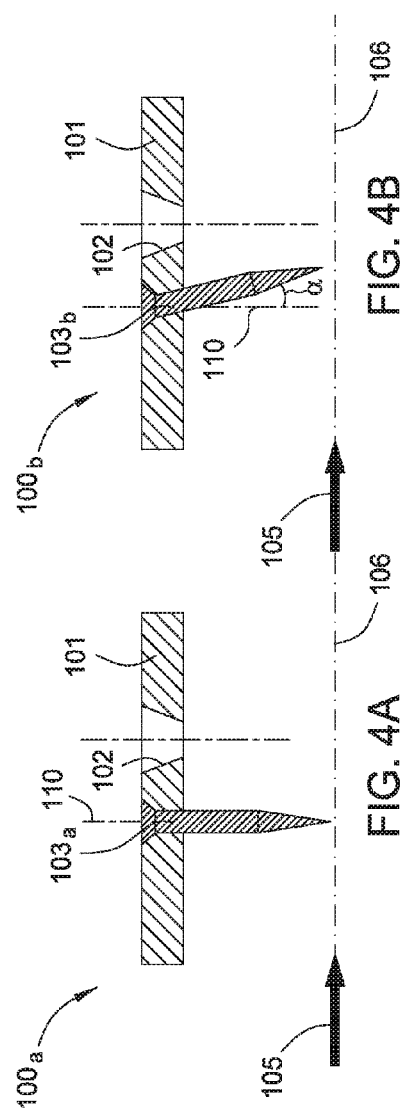
FIG. 4A
FIG. 4B
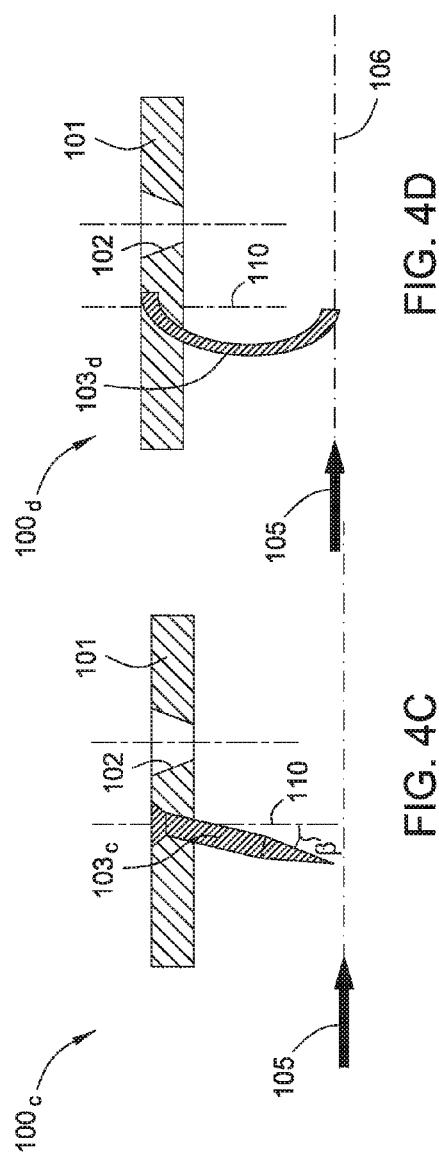
FIG. 4C
FIG. 4D

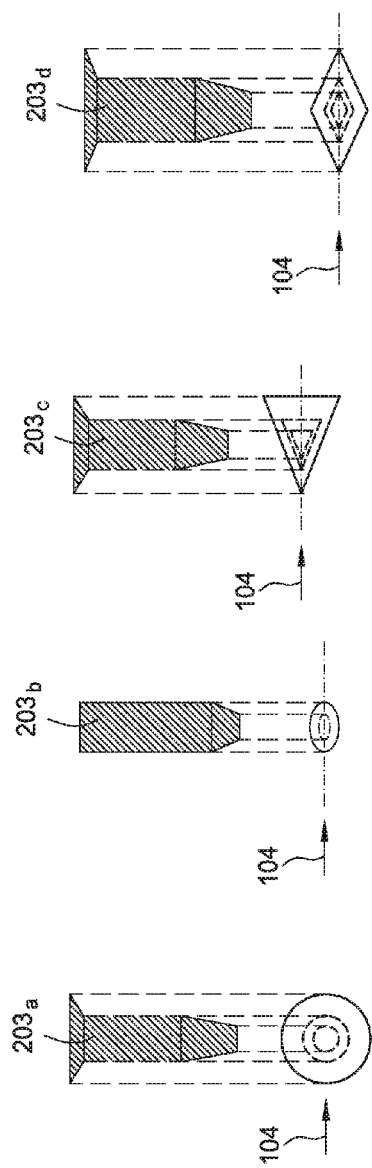

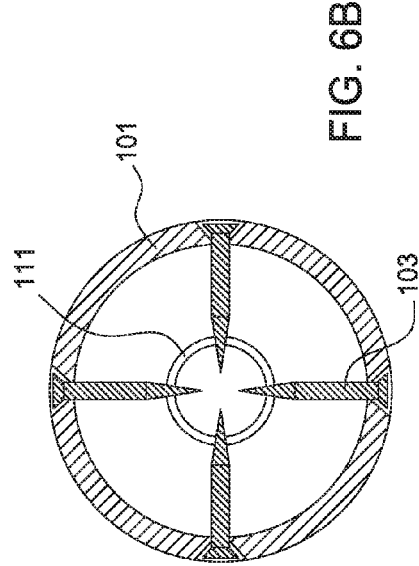
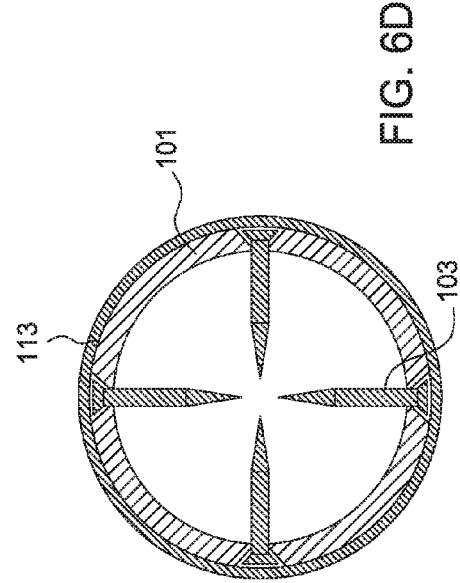
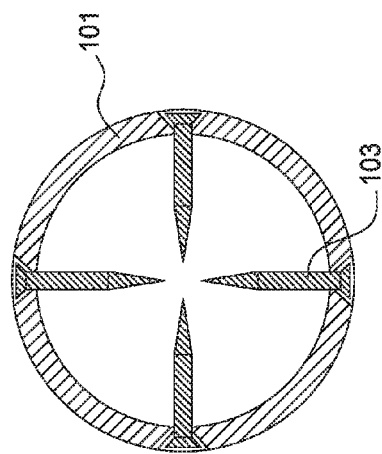
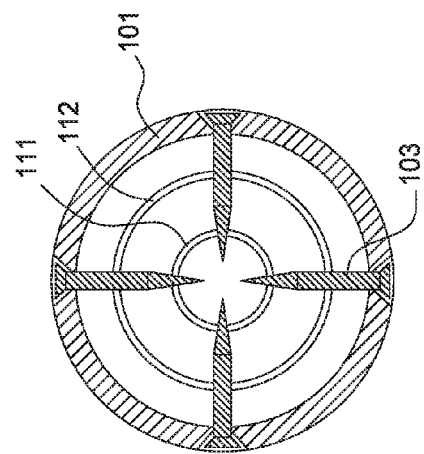
FIG. 6A
FIG. 6B
FIG. 6C
FIG. 6D

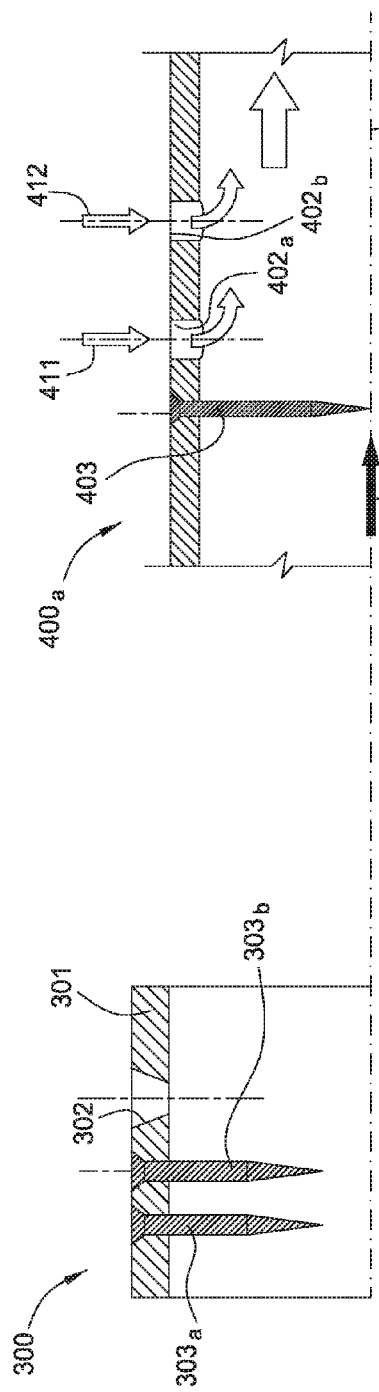
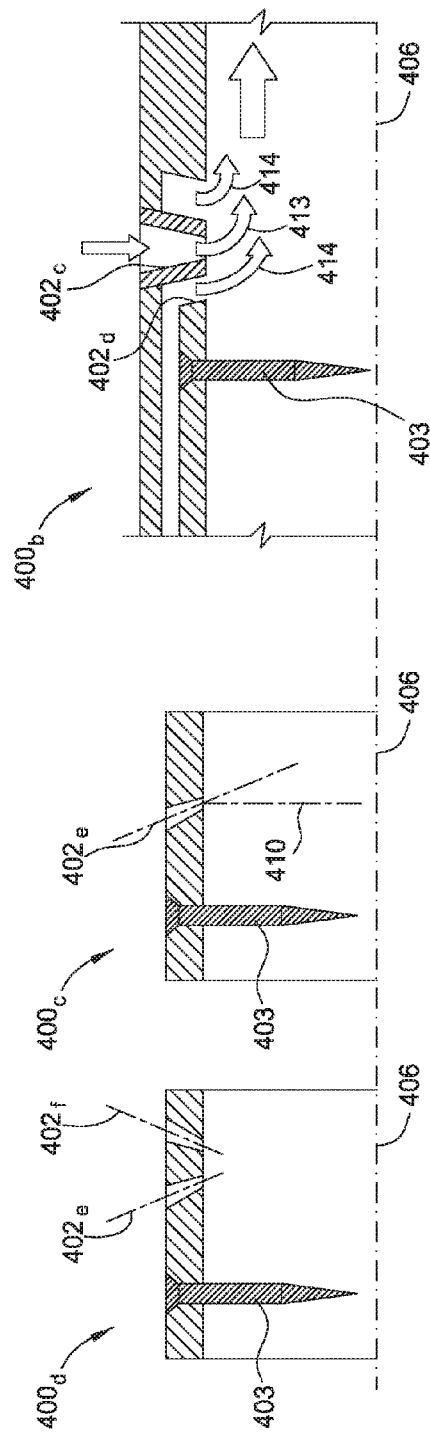
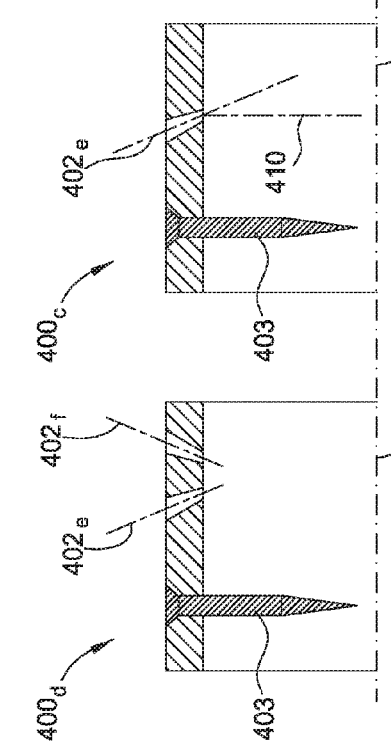

REACTIVE FLOW STATIC MIXER WITH CROSS-FLOW OBSTRUCTIONS

BACKGROUND OF THE INVENTION

Field of the Invention

Embodiments of the present invention relate to a mixing apparatus for mixing fluid components, such as the mixing of phosgene and amine in a reactive chemical process.

Description of the Related Art

The field of conventional mixing devices can be roughly divided into two main areas: dynamic or mechanical mixers and static mixers. Dynamic or mechanical mixers rely on some type of moving part or parts to ensure the desired or thorough mixing of the components. Static mixers generally have no prominent moving parts and instead rely on flow profiles and pressure differentials within the fluids being mixed to facilitate mixing. The current disclosure is mostly directed to a static mixer but could also be used in combination with dynamic mixers.

Isocyanates are molecules characterized by N=C=O functional groups. The most widely used isocyanates are aromatic compounds. Two aromatic isocyanates are widely produced commercially, namely, toluene diisocyanate (TDI) and methylene diphenyl diisocyanate (MDI). Isocyanates may be reacted with polyols to form polyurethanes. Major polyurethane applications are rigid foams, which are good insulators and are heavily used in appliance, automotive and construction businesses; and flexible foams which may be used in mattresses and furniture applications. In addition aliphatic isocyanates such as hexamethylene diisocyanates are also widely produced and used in special applications such as abrasion and UV resistant coatings.

Mixing is important in isocyanate production. The isocyanate product quality and yield are dependent on a multistep chemical reaction network. In the first step of the process, two continuous streams of reactants (amine and phosgene) are mixed. Secondary reactions like the reaction between phosgenation products and amine to form ureas and other urea derivatives ultimately reduce the quality of the product composition. While the production of isocyanates is desired, secondary reactions lead to the creation of undesired products. Some of these secondary reactions are believed to create products such as ureas and urea derivatives like carbodiimides, and uretonimines. The overall chemical reaction can be depicted as follows:

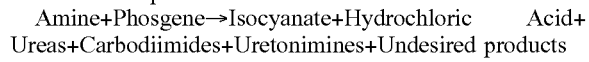

Amine+Phosgene→Isocyanate+Hydrochloric Acid+Ureas+Carbodiimides+Uretonimines+Undesired products While many known and unknown factors control the quality of the principal reaction, an increase of the ratio of phosgene to amine, a dilution of amine in a solvent, or an improved mixing minimizes the formation of undesired by-products. Some of the undesired byproducts may be solids and may be associated with fouling in process equipment.

Consequently, mixer designs with improper mixing can result in lower overall yield of the desired product or can generate a product that clogs or fouls the reactor system leading to down time and/or increased maintenance costs.

FIG. 1 schematically illustrates phosgene concentration within a static mixer of the prior art. FIG. 1 illustrates a partial sectional view of a cylindrical conduit 3 where a phosgene flow 1 goes from the left to the right and an amine flow 2 is injected into the phosgene flow 1 from a jet 4 formed through the cylindrical conduit 3. As amine traverses and reacts with the phosgene, principal and secondary reactions occur. A circle 5, which is located at the distance L where amine flow 1 enters, illustrates a region on the downstream side of the jet 4 where the phosgene concentration is relatively low (near zero). Because phosgene and amine reactions are exothermic, the regions surrounding circle 5 have increased temperature. The low concentration of phosgene and increased temperature promote the formation of undesirable secondary reactions and production of by-product.

It would be desirable to have a static mixer that improves phosgene and amine mixing thus limiting the production of undesired by-products.

SUMMARY OF THE INVENTION

Embodiments of the present invention relate to a static mixing apparatus that can be used alone or in combination with dynamic mixers.

One embodiment of the static mixing apparatus provides a mixing conduit comprising a cylindrical sidewall defining an inner volume, wherein one or more jets are formed through the cylindrical sidewalls to the inner volume and one or more flow obstructions are disposed in the inner volume, wherein each flow obstruction is aligned upstream from an associated aperture to improve the cross flow with respect to jet penetration, and jet mixing and reduce back-mixing in the mixing conduit.

Another embodiment of the present invention provides a static mixer comprising one or more fluid receiving conduits defining one or more outer walls of an annular chamber and a mixing conduit of the present invention disposed in a first conduit to define at least an inner wall of the annular chamber, wherein the annular chamber is in fluid communication with the one or more jets of the mixing conduit.

BRIEF DESCRIPTION OF THE DRAWINGS

So that the manner in which the above recited features of the present invention can be understood in detail, a more particular description of the invention, briefly summarized above, may be had by reference to embodiments, some of which are illustrated in the appended drawings. It is to be noted, however, that the appended drawings illustrate only typical embodiments of this invention and are therefore not to be considered limiting of its scope, for the invention may admit to other equally effective embodiments.

FIGS. 4A-4D schematically illustrate various embodiments of mixing conduits having obstructions mounted at different configurations.

FIGS. 5A-5G schematically illustrate various embodiment of obstructions for using in a mixing conduit such that the shape of the obstructions in radial direction further streamlines the cross-flow according to embodiments of the present invention.

FIGS. 6A-6D schematically illustrate various mechanisms for mounting obstructions in a mixing conduit according to embodiments of the present invention.

FIG. 9 schematically illustrates a mixing conduit with multiple rows of obstructions according to one embodiment of the present invention.

FIGS. 10A-10D schematically illustrate mixing conduits having complex jets designs according embodiments of the present invention.

To facilitate understanding, identical reference numerals have been used, where possible, to designate identical elements that are common to the figures. It is contemplated that elements disclosed in one embodiment may be beneficially utilized on other embodiments without specific recitation.

DETAILED DESCRIPTION

Embodiments of the present invention relate to a static mixing apparatus for mixing components, in applications with or without chemical reactions, where mixing is rate-limiting step and may cause undesired product formation. Particularly, embodiments of the present invention provide a mixing apparatus for mixing fluid components such as phosgene and amine during a highly reactive chemical reaction.

Static mixers of the present invention are designed to provide rapid mixing in industrial reactive processes, such as the reaction of MDA with phosgene to form MDI. Embodiments of the present invention provide static mixers that enable the phosgene to engulf the amine stream and minimize secondary reactions. The energy used to mix the fluid comes from the pressure drop in a mixing device. Static mixers of the present invention improve jet mixing process which enables increased production rates while maintaining reasonable pressure drop and improving product quality.

Embodiments of the present invention create a velocity profile in a first flow, typically a main cross-flow, as the first flow passes through a conduit and intersects with a second flow injected into the conduit by one or more jets formed through the conduit. In one embodiment, the velocity profile in the first flow is made by one or more flow obstructions placed upstream in the conduit. The one or more flow obstructions direct the first flow, such as phosgene, around the second flow, such as amine. The flow obstructions minimize the phosgene-deficient regions close to the amine jets and let the phosgene better engulf the amine stream.

One embodiment of the present invention provides a static mixer having a conduit with at least one aperture formed through a circumference of the conduit, and at least one obstruction disposed in the conduit upstream to the at least one aperture. During mixing, a first flow component flows through the conduit passing the at least one obstruction then encounters a second flow entering the conduit through the associated at least one aperture.

Figure 2:
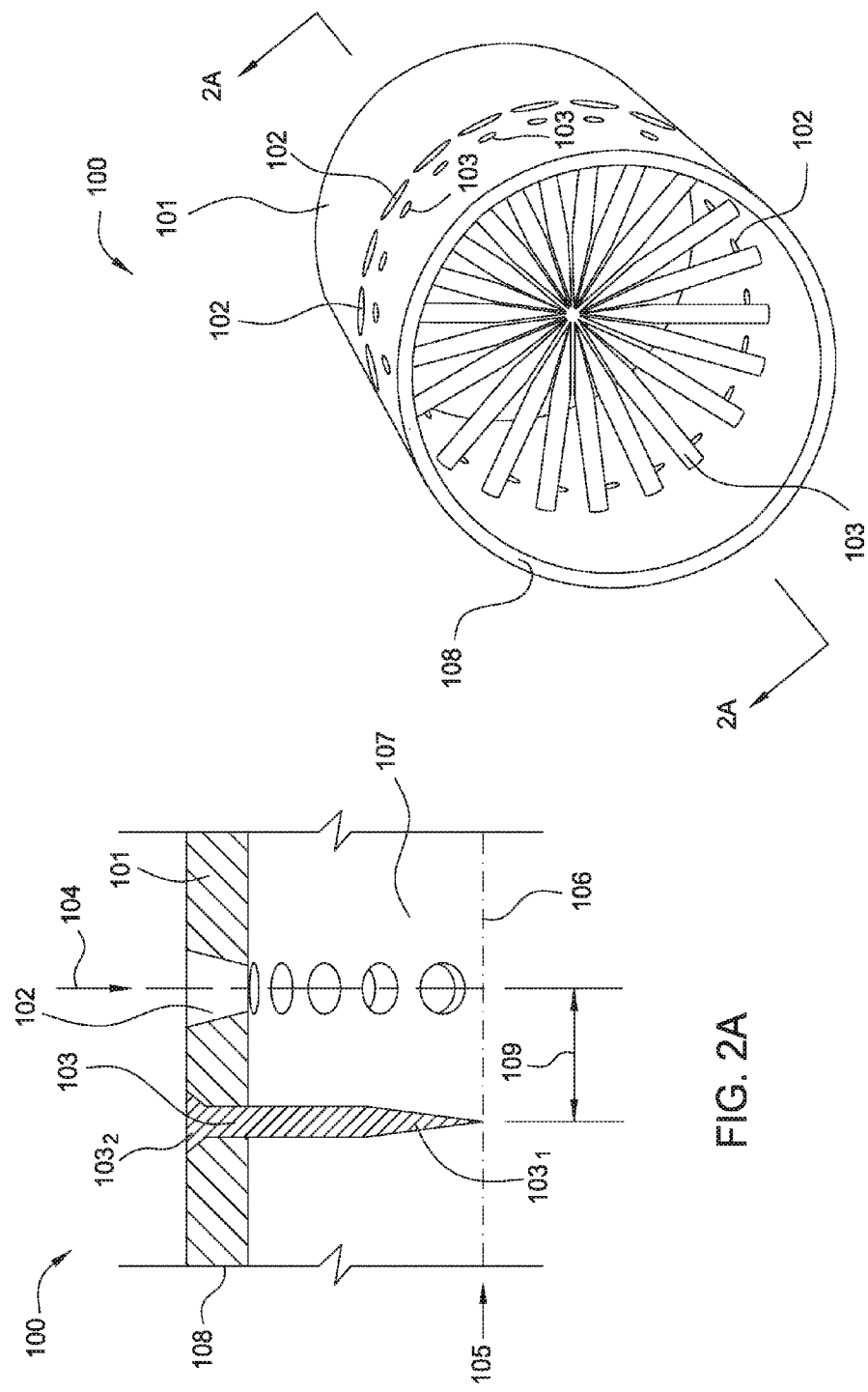
FIG. 2A is a partial sectional view of a mixing conduit for a static mixer according to one embodiment of the present invention.
FIG. 2B is a perspective view of the mixing conduit of FIG. 2A.

FIG. 2A is a partial sectional view of a mixing conduit 100 for a static mixer according to one embodiment of the present invention. FIG. 2B is a perspective view of the mixing conduit 100 of FIG. 2A.

The mixing conduit 100 comprises a cylindrical sidewall 101 defining an inner volume 107. A first flow 105 is configured to enter the inner volume 107 from an inlet end 108 of the mixing conduit 100. The mixing conduit 100 has a central axis 106.

A plurality of apertures 102 are formed through the cylindrical sidewall 101 around a circumference of the mixing conduit 100. The plurality of apertures 102 are configured to inject a second flow 104 to the inner volume 107 of the mixing conduit 100. In one embodiment, the plurality of apertures 102 are evenly distributed around the circumference of the mixing conduit 100.

FIG. 2A shows that each aperture 102 has a tapered shape. The tapered shape of the apertures 102 create a velocity profile in the second flow 104 as the second flow 104 enters the mixing conduit 100 so that the second flow 104 can penetrate closer to the central axis 106. However, other designs of the aperture 102 may also be used. U.S. patent application Ser. No. 11/658,193, filed Jul. 7, 2005, published as US Publication 2008/0087348, having a least partial common inventorship and directing to a static mixer having tapered apertures, is incorporated herein by reference.

The mixing conduit 100 further comprises a plurality of spokes 103 disposed between the plurality of apertures 102 and the inlet end 108 of the mixing conduit 100. Each of the plurality of spokes 103 is aligned with an associated aperture 102 to create a flow obstruction in the first flow 105 before the first flow reaches the associated apertures 102.

In one embodiment, the plurality of spokes 103 are inserted into the mixing conduit 100 through the cylindrical sidewall 101. Each spoke 103 may have an inner end $103_1$ and an outer end $103_2$. The inner end $103_1$ is smaller than the outer end $103_2$ so that after the inner end 103a enters the mixing conduit 100 by penetrating the cylindrical sidewall 101, the outer end $103_2$ plugs the opening to seal the mixing conduit 100. Because each spoke 103 is directly aligned with an associated aperture 102, the spoke 103 creates a first flow velocity decrease upstream of the entrance of the second flow 104 from each aperture 102, therefore, allowing the second flow 104 to penetrate deeper inside the inner volume 107 and improving mixing.

Various factors may be adjusted to improve mixing according to the processing condition. For example, the distance 109 between the apertures 102 and the spokes 103, the size of each spoke 103, mounting angle of the spokes 103, the length of each spoke 103, the shape of the spoke 103, the design of the associated aperture 102, can be adjusted.

During mixing, the first flow 105 enters the mixing conduit 100 from the inlet end 108 and encounters the plurality of spokes 103. The plurality of spokes 103 mask the second flow 104 downstream from the cross-flow of the first flow 105 and increase the velocity of the first flow 105 in the spaces between the second flow from the apertures 102.

Figure 3:
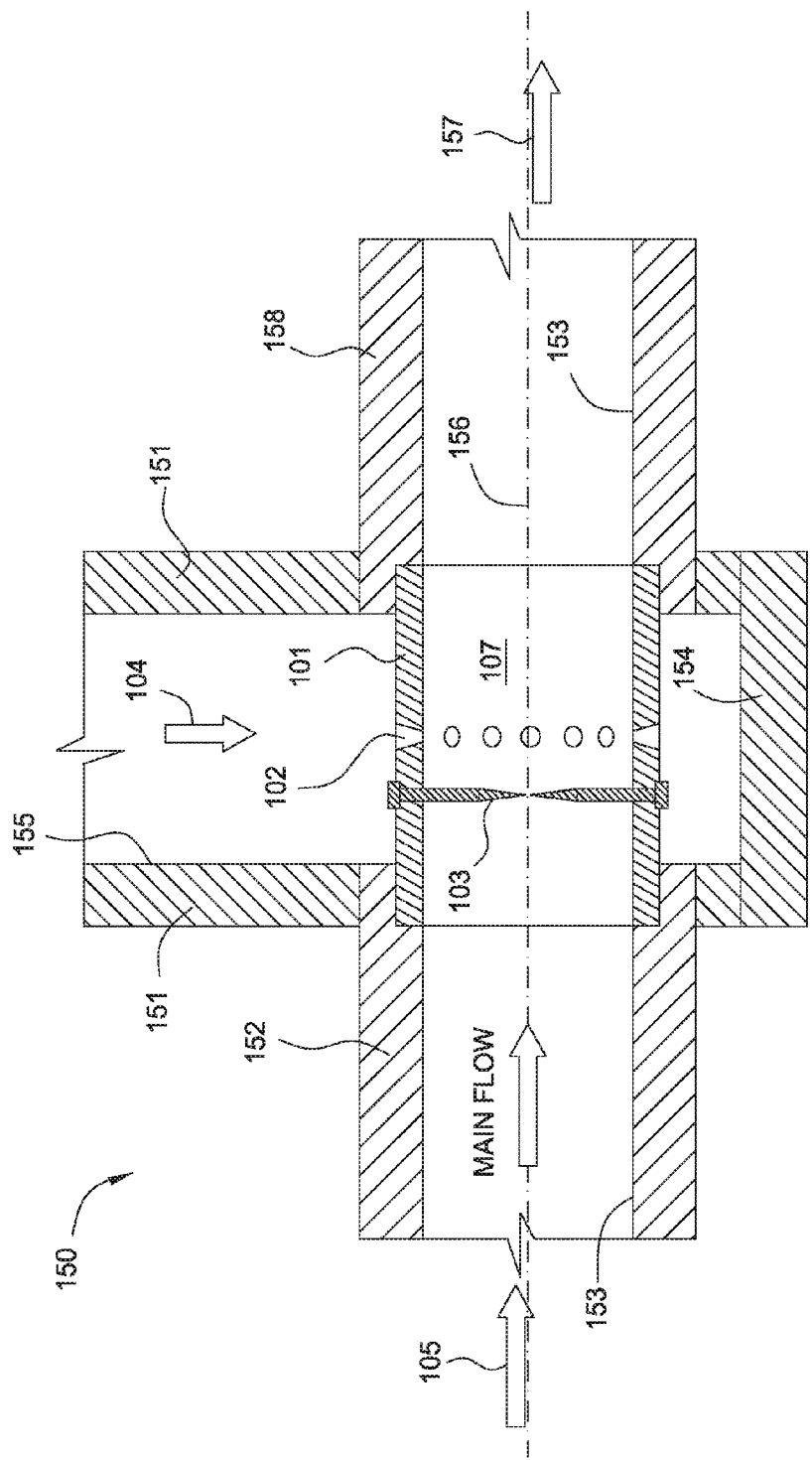
FIG. 3 is a sectional view of a static mixer according to one embodiment of the present inventions.

FIG. 3 is a sectional view of a static mixer 150 according to one embodiment of the present. The static mixer 150 defines a cross-flow chamber formed by a second-flow conduit 155 attached within a first-flow conduit 153 having a longitude axis 156. A mixing conduit 100, as shown in FIG. 2A, is disposed in the first-flow conduit 153 so that the mixing conduit 100 is co-axial with the first-flow conduit 153 and the plurality of apertures 102 fluidly connect the second-flow conduit 155 and the inner volume 107 of the mixing conduit 100. The mixing conduit 100 defines at least an inner wall of the annular chamber formed by conduit walls 154 and 155, wherein the annular chamber is in fluid communication with the one or more jets of the mixing conduit 100. The mixed flow 157 exits through an outlet end 158 of the first-flow conduit 153 co-axial with mixing conduit 100.

The mixing conduit 100 isolates the first-flow conduits 153 from the second-flow conduit 155 so that the second flow 104 can only mix with the second flow 105 via the plurality of apertures 102 in the mixing conduit 100. The first flow 105 enters the mixing conduit 100 from the inlet end 152 of the first-flow conduit 153, passes the plurality of spokes 103, then mixes with the second flow 104 entering the mixing conduit 100 from the second conduit 155 through the plurality of apertures 102. The mixed flow 157 exits the mixing conduit 100 through the outlet end 158. In one embodiment the flow area within first-flow conduit 153 maybe varying to impart, for example a reducing and expanding flow profile.

It should be noted that the mixing conduit 100 may be used with other mixing devices. Various mixing conduits may be used with a static mixer of the present invention.

FIGS. 4A-4D schematically illustrate various embodiments of mixing conduits having various obstructions mounted at different angles.

FIG. 4A illustrates a mixing conduit 100*a* similar to the mixing conduit 100 of FIG. 2A. The mixing conduit 100*a* having a plurality of spokes 103*a* mounted parallel to a plane 110 that is perpendicular to the central axis 106 of the mixing conduit 100*a*. FIG. 4B illustrates a mixing conduit 100*b* having a plurality of spokes 103*b* mounted at an angle α relative to the plane 110. The ends of the plurality of spokes 103*b* are angled towards the downstream direction. FIG. 4C illustrates a mixing conduit 100*c* having a plurality of spokes 103*c* mounted at an angle β relative to the plane 110. The ends of the plurality of spokes 103*d* are angled towards the upstream direction. FIG. 4D illustrates a mixing conduit 100*d* having a plurality of curved spokes 103*d* mounted relative to the plane 110. The plurality of spokes 103*d* are angled towards the upstream direction at the outer region of the conduit 100*d* and angled towards the downstream direction near the center of the conduit 100*d*. The angled orientation in conjunction with the shape of the obstructions can further provide improved cross-section interaction between the first flow and the second flow.

FIGS. 5A-5G schematically illustrate various embodiments of spokes for using in a mixing conduit according to embodiments of the present invention. Each FIG. 5A-5G includes a sectional view and a top view of a spoke. FIG. 5A illustrates a spoke 203*a* having a circular crossection and a partially tapered end. FIG. 5B illustrates a spoke 203*b* having an oval cross-section and a partially tapered end without a head. FIG. 5C illustrates a spoke 203*c* having a triangular cross-section. FIG. 5D illustrates a spoke 203*d* having a diamond shaped cross-section. FIG. 5E illustrates a spoke 203*e* having a diamond cross-section (kite shaped) without any tapered end. FIG. 5F illustrates a spoke 203*f* having a tear-drop shaped cross-section and a fully-tapered shape. FIG. 5G illustrates a spoke 203*g* having an oval cross-section and the spoke 203*f* is larger at an inner end that an outer end.

FIGS. 6A-6D schematically illustrate various mechanisms for mounting obstructions in a mixing conduit according to embodiments of the present invention. In FIG. 6A, the spokes 103 are simply inserted into the sidewall 101 of the mixing conduit 100 and secured therein. The spoke 103 has an increased diameter on the one end (103*b*) attached to mixing conduit 100 in FIG. 2A to prevent it from being moved into the mixing conduit 100. In FIG. 6B, the plurality of spokes 103 are coupled to a center ring 111 inside the mixing conduit 100. The center ring 111 holds the plurality of spokes 103 in place. In one embodiment, the center ring 111 may be a center plate as shown in FIG. 7B. In FIG. 6C, two concentric center rings 111, 112 inside the conduit 100 are used to secure the plurality of spokes 103. In FIG. 6D, a retaining ring 113 disposed outside the sidewall 101 is used to prevent the spokes 103 from popping out of the mixing conduit 100.

Figure 7C:
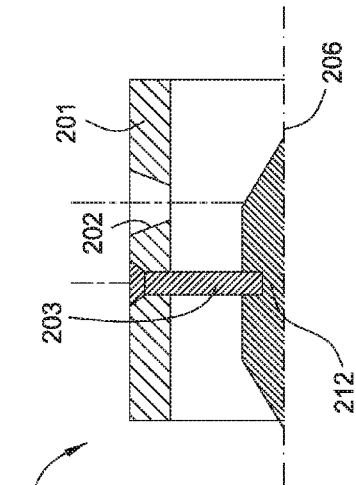
FIG. 7C illustrates mounting of flow obstructions on a torpedo shaped central obstruction.
Figure 7A:
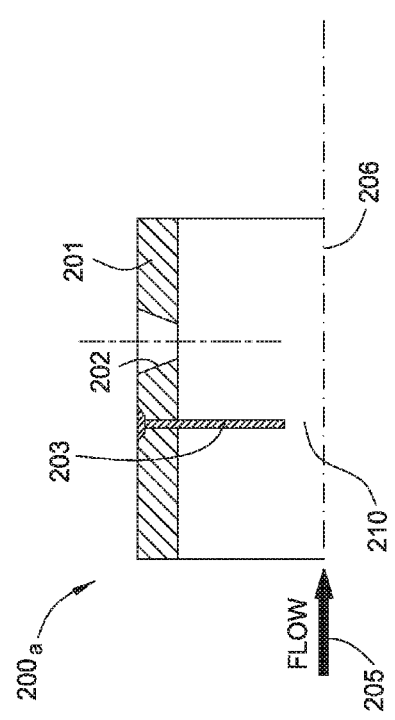
FIGS. 7A-7B schematically illustrate a mixing conduit with various configurations near a center axis according to embodiments of the present invention.
Figure 7B:
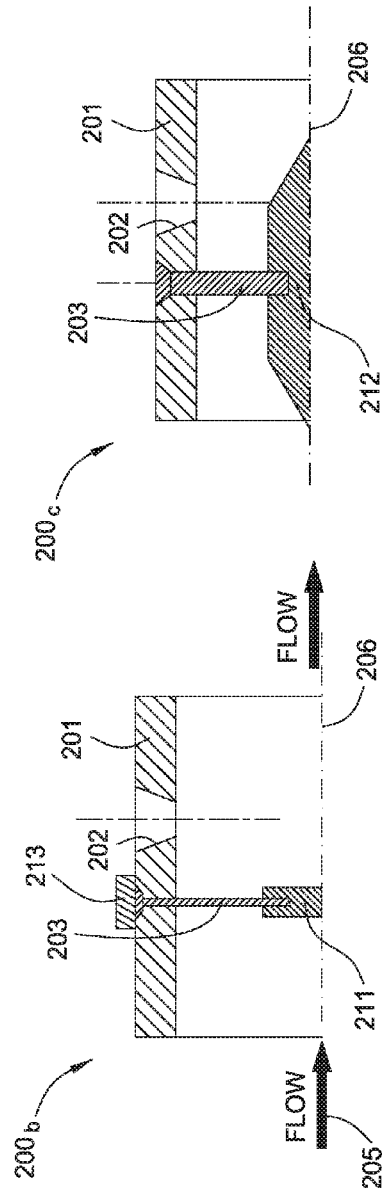

FIGS. 7A-7C schematically illustrate mixings conduit with various configurations near a center axis according to embodiments of the present invention.

FIG. 7A illustrates a mixing conduit 200*a* having a plurality of spokes 203 positioned upstream to a plurality of apertures 202. The spokes 203 do not reach a central axis 206 of the mixing conduit 200*a* leaving a circular gap 210 near a center region in the mixing conduit 200*a*. There is no obstruction to cross-flow 205 near the center of the mixing conduit 200*a*.

FIG. 7B illustrates a mixing conduit 200*b* having a disk 211 secured to the plurality of spokes 203 near the center of the mixing conduit 200*b*. A side view of the mixing conduit 200*b* is shown in FIG. 8A. The disk 211 not only secures the spokes 203 but also provides additional obstructions to the cross flow 205. The obstruction from the disk 211 further increases the velocity of the cross flow 205 because of reduced cross-sectional area in the mixing conduits 200*b*. The disk 211 also creates a deficit of the cross flow 205 near the central axis 206 to improve mixing in the situations when the flow from aperture 202 cannot reach the central axis 206. In one embodiment, a retaining ring 213 is disposed outside a cylindrical wall 201 of the mixing conduit 200*b* for securing the spokes 203.

FIG. 7C illustrates a mixing conduit 200*c* having a streamlined axial flow obstruction or a torpedo 212 secured to the plurality of spokes 203 near the center of the mixing conduit 200*c*. The torpedo 212 may have a cylindrical middle section and tapered ends. The torpedo 212 provides the same function as the disk 211 in FIG. 7B. Additionally, the torpedo 212 also provides obstruction along a longitude of the mixing condition 200*c* so that the effect of obstructions from the spokes 203 and torpedo 212 extends further downstream. Detailed description of the torpedo design may be found in U.S. patent application Ser. No. 12/725,262 filed on Mar. 16, 2010, by at least a partial common inventorship, which is incorporated herein by reference.

Figure 8C:
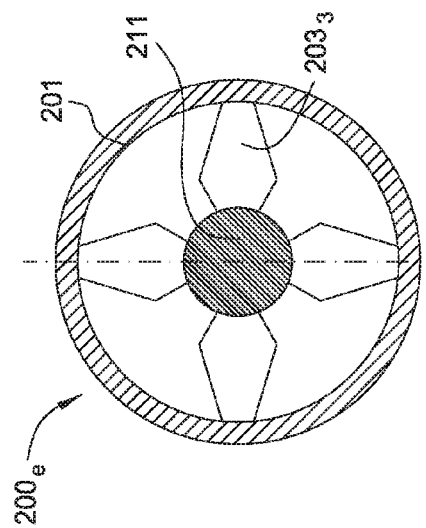
FIGS. 8A-8C schematically illustrate various mixing conduits having a central disk coupled to flow obstructions in vane like shapes directing the cross-flow according to embodiments of the present invention.
Figure 8B:
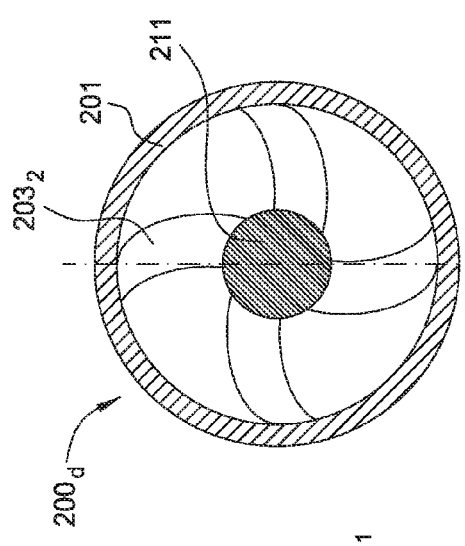
Figure 8A:
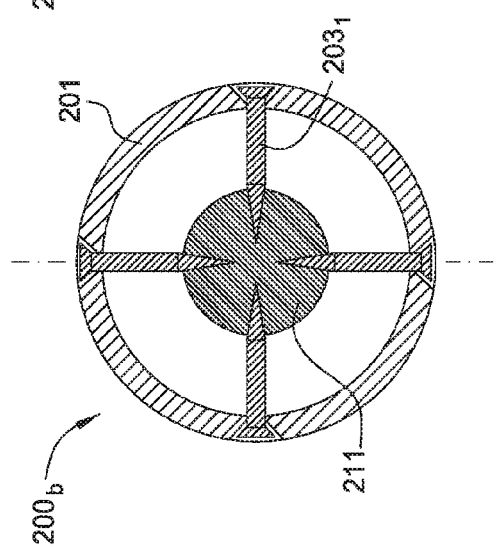

FIGS. 8A-8C schematically illustrate various mixing conduits having a central disk coupled to obstructions according to embodiments of the present invention. When a central disk, such as disk 211 in FIGS. 8A and 7B, is used, various spokes may be used to provide a tailored function. In FIG. 8A, straight spokes $203_1$ with tapered shape are coupled to the disk 211 in the mixing conduit $200_b$. In FIG. 8B, curved vanes $203_2$ are used in a mixing conduit $200_c$. In FIG. 8C, expanding and contracting vanes $203_3$ are used a mixing conduit $200_d$. These vanes act as flow directors and can be designed to provide an advantageous velocity profile.

FIG. 9 schematically illustrates a mixing conduit 300 with complex obstructions according to one embodiment of the present invention. Two or more sets of spokes may be used in the mixing conduit 300. As shown in FIG. 9, two sets of spokes 303*a*, 303*b* are disposed upstream to a plurality of apertures 302 formed through sidewall 301 of the mixing conduit 300. In one embodiment, each spoke 303*a*, 303*b* may be aligned with the perspective aperture 302. In another embodiment, the spokes 303*a*, 303*b* may be such that the spokes are not exactly aligned with respect to each other. In further embodiments, the sets of spokes vary in shape and/or dimension.

Embodiments of spokes described above may be used in combination of various aperture designs. FIGS. 10A-10D schematically illustrate mixing conduits having complex jets according embodiments of the present invention.

FIG. 10A schematically illustrates a sectional view of a mixing conduit 400a having a plurality of spokes 403 positioned upstream to two sets of apertures 402a, 402b. The apertures 402a is positioned upstream to the apertures 402b, which may be used to cool and or dilute the second flow with a solvent or with components in main flow. A cross flow 405 will be mixed with two sets of jet stream 411, 412 from the apertures 402a, 402b respectively at different longitudinal locations. The plurality of spokes 403 provide obstructions to both sets of apertures 402a, 402b.

FIG. 10B schematically illustrates a sectional view of a mixing conduit 400b having a plurality of spokes 403 positioned upstream to two sets of apertures 402c, 402d. The apertures 402c are formed inside the apertures 402d. Jet stream 413 from the apertures 402c may have different flow rate than jet stream 414 from the aperture 402d, which may be used to cool and or dilute the second flow with a solvent or with components in main flow. A cross flow 405 will be mixed with two sets of jet stream 413, 414 at substantially the same longitudinal locations. The plurality of spokes 403 provide obstructions to both sets of apertures 402c, 402d.

FIG. 10C schematically illustrates a sectional view of a mixing conduit 400c having a plurality of spokes 403 positioned upstream a plurality of apertures 402e relatively angled to a plane 410 perpendicular to the central axis 406 of the mixing conduit 400c.

FIG. 10D schematically illustrates a sectional view of a mixing conduit 400d having a plurality of spokes 403 positioned upstream to two sets of apertures 402e, 402f. The mixing conduit 400d is similar to the mixing conduit 400a except the apertures 402e and 402f are tilted at different angles.

Detailed description of other jets that may be combined with obstructions described herein may be found in U.S. patent application Ser. No. 12/725,266 filed on Mar. 16, 2010, by at least a partial common inventorship, which is herein incorporated by reference.

EXAMPLE

Embodiments of the present inventions are used in mixing phosgene as the first flow with amine as the second flow as in MDI production process. The static mixer's performance is determined by the level of undesirable by-products, such as uretoneimines, and the pressure losses in the static mixer. In one embodiment, the second flow comprises at least one of methylene diphenyl diamine, toluene diamine, and hexamethylene diamine. Mixing conduits with flow obstructions according to embodiments of the present invention modifies velocity profiles in the first flow such that an amount of ureas, carbodiimides, and uretonimines formed are less than in a method where no obstructions are disposed in the inner volume. A comparison of performance of several mixers is given in Table 1.

Figure 1:
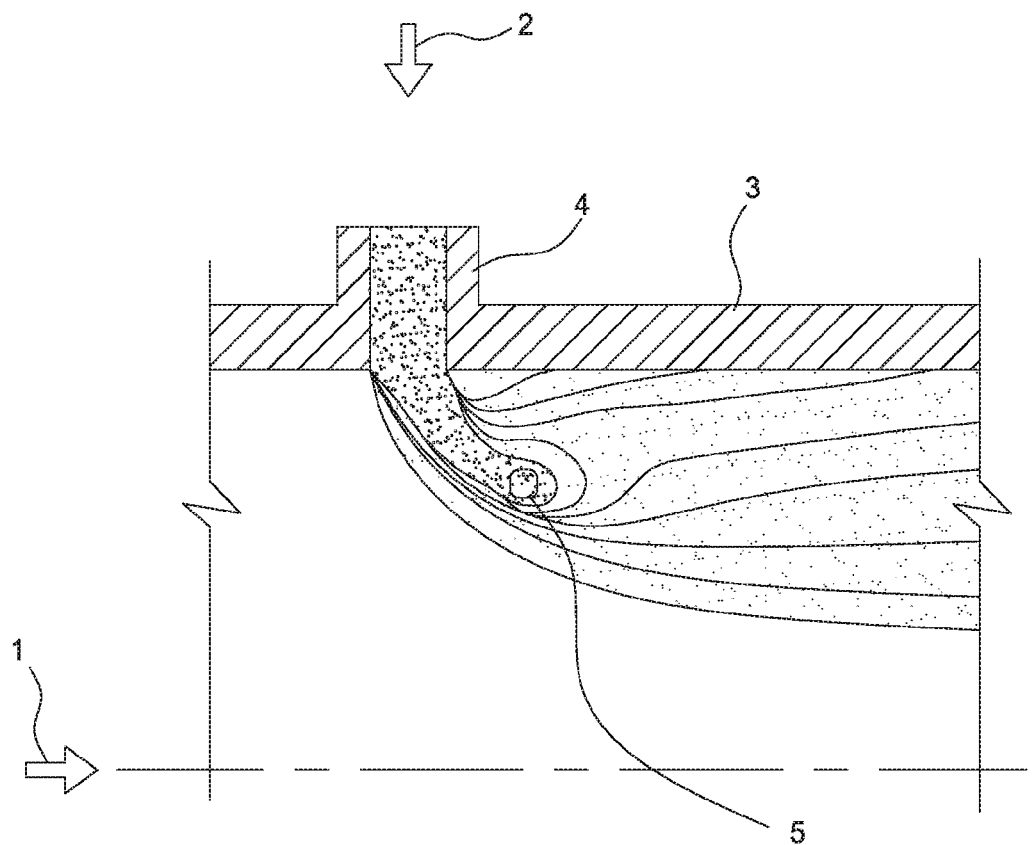
FIG. 1 schematically illustrates phosgene concentration within a static mixer of prior art used in mixing phosgene and amine.

For the mixers showing in Table 1, the number, size and shape of the amine jets were held constant. Option 1 represents the prior art with no upstream flow obstruction, as shown in FIG. 1. Option 2 represents the mixer shown in FIG. 7B. Option 2 reduces the undesired by-product, uretonimine, with only a slight change in the pressure loss of the cross-flowing phosgene stream compare to option 1. Option 3 represents the design shown in FIG. 7A. Option 3 has less improvement in uretonimine levels but the change in pressure drop is also smaller. Option 4 is the spike mixer shown in FIGS. 2A-2B. Option 4 results in a higher reduction in uretonimine compared with the previous Options 2 and 3. Option 5 represents the design shown in FIG. 7C. Option 5 gives both the lowest uretonimine but also has the greatest phosgene pressure drop due to the dominant obstruction of the centeral cross-flow.

TABLE 1

Relative Comparison of Selectivity and Pressure Drop

|  | Option 1 No Obstruction | Option 2 Disc with Spokes | Option 3 Spokes | Option 4 Tapered Spokes | Option 5 Spokes Annulus |
|---|---|---|---|---|---|
| Relative uretonimine | 1 | 0.89 | 0.96 | 0.88 | 0.80 |
| Amine pressure drop | 1 | 1.02 | 1.00 | 1.01 | 1.00 |
| Phosgene pressure drop | 1 | 1.10 | 1.04 | 1.08 | 1.23 |

While the foregoing is directed to embodiments of the invention, other and further embodiments of the invention may be devised without departing from the basic scope thereof.

What is claimed is:

1. A method for mixing phosgene with at least one of methylene diphenyl diamine, toluene diamine, and hexamethylene diamine in a mixing conduit, the method comprising:
    a) providing a mixing conduit comprising
        i) a cylindrical sidewall defining an inner volume;
        ii) plurality of apertures formed through the cylindrical sidewall along a circumference of the cylindrical sidewall, said apertures connecting to the inner volume of the cylindrical sidewall;
        iii) a plurality of spokes inserted into the inner volume along the circumference of the cylindrical sidewall, and wherein each of the plurality of spokes is aligned with and entirely upstream of an associated aperture to create a flow obstruction upstream of said associated aperture, said spokes being characterized in that each spoke has a cross-section in the shape of one of a circle, oval, triangle, diamond, non-symmetrical diamond, or tear-drop; and wherein the plurality of spokes are coupled to a disk substantially concentric to the cylindrical sidewall of the mixing conduit;
    b) flowing a first flow comprising phosgene through the inner volume, along a longitude of the mixing conduit and sequentially past said spokes and then past said apertures; and
    c) flowing a second flow comprising at least one of methylene diphenyl diamine, toluene diamine, and hexamethylene diamine though said apertures and into said inner volume to form jets of said second flow into said first flow.

2. The method of claim 1, wherein each spoke is tapered having a large end coupled to the cylindrical sidewall and a small end near a central axis of the mixing conduit.

3. The method of claim 1, wherein said apertures comprise at least one tapered aperture having a large opening outside the mixing conduit and a small opening inside the mixing conduit.

4. The method of claim 1, wherein an additional aperture is disposed adjacent is disposed adjacent each of the plurality of apertures downstream on a longitudinal axis of the cylindrical sidewall.

5. The method of claim 1, wherein said plurality of apertures comprises at least one aperture tilted at an angle relative to a plane perpendicular to a longitudinal axis of the mixing conduit.

6. The method of claim 1, wherein the spokes are mounted at an angle relative to a plane perpendicular to a longitudinal axis of the mixing conduit.

* * * * *